(12) United States Patent
Boeufgras et al.

(10) Patent No.: US 6,611,765 B2
(45) Date of Patent: *Aug. 26, 2003

(54) SYSTEM FOR VALIDATION AND INTERPRETING RESULTS OF ANTIMICROBIAL SUSCEPTIBILITY TESTS OF MICRO-ORGANISMS

(75) Inventors: Jean-Marc Boeufgras, Vaux en Bugey (FR); Annie Lazzarini, Ambronay (FR); Michel Peyret, Lyons (FR)

(73) Assignee: Biomerieux, 69280 Marcy-L'Etoile (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 86 days.

(21) Appl. No.: 09/230,231

(22) PCT Filed: May 4, 1998

(86) PCT No.: PCT/EP98/02791
§ 371 (c)(1),
(2), (4) Date: May 10, 1999

(87) PCT Pub. No.: WO98/53095
PCT Pub. Date: Nov. 26, 1998

(65) Prior Publication Data
US 2001/0039031 A1 Nov. 8, 2001

(30) Foreign Application Priority Data
May 16, 1997 (EP) .............................. 97410052

(51) Int. Cl.⁷ ............................ G06F 7/20; G06F 9/455; G06N 7/00; C12Q 1/18
(52) U.S. Cl. .......................... 702/19; 707/104.1; 703/5; 435/32; 435/33; 435/34
(58) Field of Search ...................... 435/32, 33, 34; 345/970; 707/6, 7, 104, 104.1; 702/19; 703/2

(56) References Cited

U.S. PATENT DOCUMENTS 4,236,211 A * 11/1980 Arvesen ..................... 364/413
4,448,534 A * 5/1984 Wertz et al. ................. 356/435
5,457,030 A * 10/1995 Badal et al. .................. 435/34

FOREIGN PATENT DOCUMENTS

| EP | 0010846 A1 | * 5/1980 | ............ C12Q/1/18 |
| EP | 0565994 A1 | * 10/1993 | ............ C12M/1/34 |
| WO | WO 90/04646 | * 5/1990 | ............ C12Q/1/18 |

OTHER PUBLICATIONS

Wertz et al. Computerized interpretation of minimum inhibitory concentration antimicrobic susceptibility testing. American Journal of Clinical Pathologists. 75 (3), pp. 312–319. (Mar. 1981).*

Xander et al. Improved computer–assisted reading of identification and shortened MIC data for reporting on urine specimens at a Berlin University hospital. Zantrabl Bacteriol. Mikrobiol. Hyg. Ser. A. 268, pp. 295–305. (1988) No month.*

Cornaglia et al. Rapid access to pharmakokinetics data and correlation between antimicrobial suscepitbility results and drug tissue distribution using a personal computer. Microbiologica 16, pp. 149–164. (1993) No month.*

Friedman et al. Computer identification of bacteria on the basis of their antibiotic susceptibility patterns. Applied Microbiology. vol. 26 (3), pp. 314–317. (Sep. 1973).*

* cited by examiner

Primary Examiner—Marjorie Moran
(74) Attorney, Agent, or Firm—Duane Morris, LLP

(57) ABSTRACT

The invention concerns a method for analyzing results of antimicrobial susceptibility tests of micro-organisms, the test consisting in summarily identifying which species the micro-organism belongs to and measuring the minimum inhibitory concentrations (CMI) of several antimicrobial agents for said micro-organism. The method uses a database classifying the micro-organism species and the resistance mechanism to various antimicrobial agents, and containing, for each species and each resistance mechanism, parameters characteristic of the frequency distribution of minimum inhibitory concentrations for a group of antimicrobial agents.

7 Claims, 4 Drawing Sheets

SYSTEM FOR VALIDATION AND INTERPRETING RESULTS OF ANTIMICROBIAL SUSCEPTIBILITY TESTS OF MICRO-ORGANISMS

The present invention relates to a method for analyzing test results of bacteria susceptibility to antibiotics in order to assist doctors in prescribing a treatment. The analysis can more generally extend to tests of antimicrobial agents on micro-organisms.

A conventional analysis method consists in performing identification and antibiogram tests on a bacterial strain present in a sample, for example the blood of a patient. The identification aims at knowing more or less precisely the bacterial species to which the studied strain belongs. It is in particular performed by a macroscopic and microscopic observation, and carrying out tests by means of specific biochemical reagents. In general, the sole knowledge of the bacterial species is not sufficient to predict the efficiency of a given antibiotic on the studied strain. Indeed, for each family of antibiotics, the strains of a same species can have different resistance mechanisms, which will not always deactivate the same antibiotics within the family. The antibiogram consists in bringing together the studied bacterial strain and different antibiotics likely to be efficient on this strain. It is based on a more or less accurate measurement of the Minimum Inhibitory Concentration (MIC) of each of the antibiotics for the studied strain, that is, the minimum antibiotic concentration for which the strain ceases development.

Expert committees establish a first MIC threshold under which the tested species is designated "susceptible", and a second threshold above which the species is designated "resistant". Between the two thresholds, the species is designated "intermediate". This is the information generally provided to doctors.

Before being used by doctors as a basis to prescribe an antibiotic treatment, the result of the antibiogram is often interpreted. The aim of this interpretation is to detect possible test errors, or risks of inconsistency between the behavior of the studied strain confronted to a given antibiotic in vitro during the test and in vivo in the patient's organism during the treatment. This approach is most often based on semi-empirical rules. For example, it enables detecting as erroneous a result "susceptible to an antibiotic" when the studied strain belongs to a species systematically resistant to this antibiotic, or resistant to a related antibiotic known as systematically more active. In some cases, it is based on the knowledge of the possible resistance mechanisms for the species to which the studied strain belongs.

It is thus possible to correct or comment the results given for some antibiotics, when some elements hint that the strain has a resistance mechanism which may express less in vitro than in the organism. This interpretation also involves notions in appreciating the risk for the patient: in case of doubt for an antibiotic, it is generally preferred to state that a strain is resistant, if there are other antibiotics available for a treatment, to which the strain has been found to be susceptible with unambiguously.

Present analysis systems perform the test in an automated way and are able to indicate, for each tested antibiotic, whether the species is resistant, intermediate or susceptible. Further, some of these systems enable an automation of part of the interpretation, especially by using a rule database. The rule databases implemented in these systems most often reproduce the semi-empirical rules conventionally used. Now, these rules are efficient only to detect and correct some predetermined error cases. A problem thus is the implementation of an interpretation method enabling detection of all error types and the provision, if possible, of their correction.

The recognition of the resistance mechanisms which may poorly express in vitro is required to correct or comment the results. The rule databases implemented in present systems are based on the classification as "susceptible", "intermediate", or "resistant", and closely depend on the list of tested antibiotics. In a great number of cases, they do not enable accurate detection of the resistance mechanism.

Further, the pairs of MIC thresholds determining the "susceptible", "intermediate", and "resistant" categories, being fixed by national expert committees, are likely to be modified in time and differ from one country to another, or even sometimes from one laboratory to another in some countries. The same occurs for recommendations concerning the required behavior in case a resistance mechanism that may poorly express in vitro shows up. Thus, different rule bases corresponding to the interpretative choices of the different national expert committees and enabling adaptation of the rules according to the laboratories have to be provided. Such rule bases are particularly complex and their development amounts to considerable work.

An object of the present invention is to provide an analysis method for susceptibility tests which is independent of the interpretative choices of expert committees, which enables detecting and correcting errors without having to forsee the error cases to process, and which provides, in most cases, an accurate indication of the resistance mechanisms of a tested strain for the different antibiotic families.

These objects are achieved by means of a method for analyzing test results of micro-organism susceptibility to antimicrobial agents, the test consisting of roughly identifying the species to which a micro-organism belongs and of measuring the minimum inhibitory concentrations (MIC) of several antimicrobial agents for this micro-organism. The method uses a database indexing the micro-organism species as well as their resistance mechanisms against different antimicrobial agents, and containing, for each species and each resistance mechanism, parameters characteristic of statistic MIC distributions for a group of antimicrobial agents.

According to an embodiment of the invention, the method includes the steps of extracting from the database the parameters of the distributions associated with the resistance mechanisms of the identified species and with the antimicrobial agents used to perform the test; comparing the MICs measured during the test with the extracted parameters; and indicating that the test is valid when the measured MICs correspond to the extracted parameters associated with at least one predetermined resistance mechanism of the identified species.

According to an embodiment of the invention, the method includes the step of indicating the predetermined resistance mechanism.

According to an embodiment of the invention, the method includes, when the test is not valid, a step of determining corrections to be performed on at least one of the measured MICs, the choice of the corrections fulfilling predetermined optimality criteria.

According to an embodiment of the invention, the method includes, when the test is not valid, the steps of extracting from the database the parameters of the MIC distributions associated with the resistance mechanisms of other species and with the antimicrobial agents used for the testing; comparing the measured MICs with the extracted parameters; and determining the species for which at least one resistance mechanism, per tested antimicrobial agent family, is identifiable based on the measured MICs.

According to an embodiment of the invention, the database contains information indicating, for species with a given resistance mechanism and for given antimicrobial agents, an in vivo resistance which may be higher than the in vitro resistance.

According to an embodiment of the invention, the distribution parameters stored in the database include the classes of MIC values and the normalized absolute frequencies, the method including, for an untested antimicrobial agent, the steps of extracting from the database the classes and absolute frequencies associated with the predetermined resistance mechanism and the untested antimicrobial agent; keeping the classes for which the absolute frequencies exceed a predetermined threshold; confronting the kept classes with two normalized MIC thresholds defining "susceptible", "intermediate", and "resistant" categories of a micro-organism; and indicating the categories located on either side of each of the normalized thresholds located in the retained classes.

The foregoing and other objects, features and advantages of the present invention will be discussed in detail in the following non-limiting description of specific embodiments in connection with the accompanying drawings.

The method according to the present invention uses a database indexing micro-organism species with their resistance mechanisms to different families of antimicrobial agents, and antimicrobial agents. For each antimicrobial agent and each resistance mechanism, the database stores parameters characteristic of a statistic distribution of minimum inhibitory concentrations (MIC). These parameters may, for example, be an average and a standard deviation, or the lower and upper limits of the distribution and an information on its shape, or the normalized absolute frequencies of each class of values. Each statistic distribution is the result of tests performed on a great number of samples of individuals of same species and of same resistance mechanism, that is, on a population representative of the species or of the resistance mechanism.

The resistance mechanisms are characterized by their inactivation spectrum on antibiotics of a same family and do not inactivate antibiotics of the other families. A family is formed of antibiotics having related biochemical structures and action modes. Accordingly, the database only stores, for a given species and a given resistance mechanism, the statistic MIC distributions associated with antibiotics of a single family.

The method according to the present invention is meant to be carried out by a computer analysis system, coupled or not to an automated antibiogram system. A software for carrying out the method according to the present invention and the database may advantageously replace the existing software and rule bases of existing analysis systems.

The drawings show histograms symbolizing normalized absolute frequency distributions of the different classes of MIC values (MIC distributions). The normalized absolute frequency of a class is, for example, the ratio of the absolute frequency of the class to the absolute frequency of the most populated class. The classes of MIC values are shown without scale and increase from left to right. Each histogram bar illustrates the number of individuals (microbial strains) inhibited by the corresponding antibiotic concentration, this number being counted down from the population not inhibited by the immediately lower concentration. At the lower limit of a MIC distribution, the most susceptible individuals start being affected by the corresponding antibiotic. At the upper limit of the distribution, the last, most resistant individuals are affected.

Figure 1:
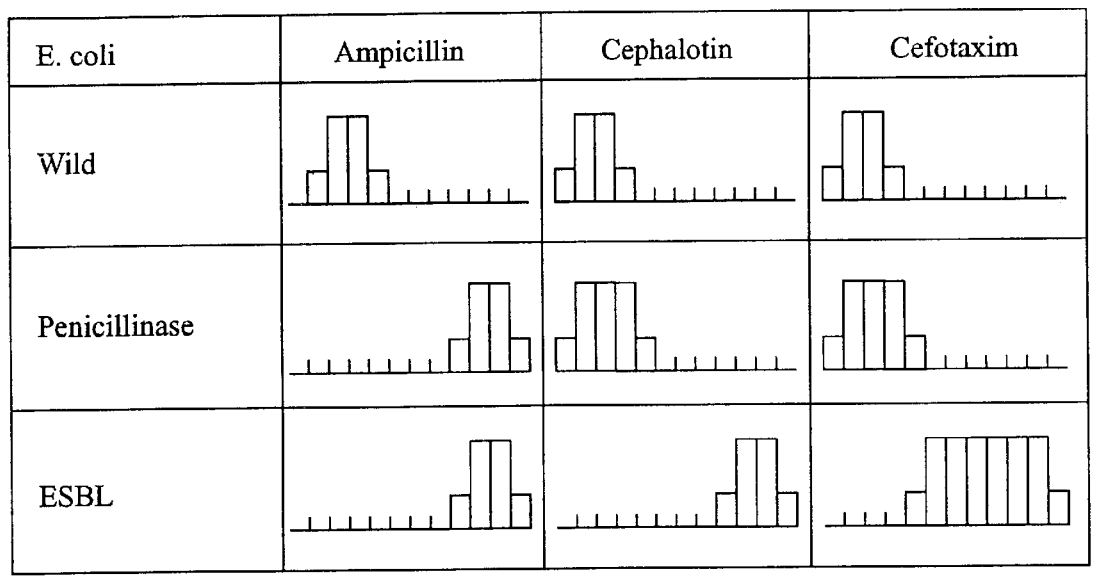
FIG. 1 illustrates an example of the contents of a database used by the method according to the present invention.

FIG. 1 illustrates an excerpt example of the data base. For species *Escherichia coli* and the beta-lactam antibiotic family, resistance mechanisms "wild", "penicillinase", and "ESBL" (extended spectrum beta-lactamase) are indexed. Among the antibiotics of the beta-lactam family, Ampicillin, Cephalotin, and Cefotaxim have been illustrated.

The strains having the wild mechanism appear to be susceptible to the three antibiotics, those having the penicillinase mechanism appear to be resistant to Ampicillin and susceptible to the two other antibiotics, and finally those with the ESBL mechanism appear to be resistant to the three antibiotics.

Figure 2:
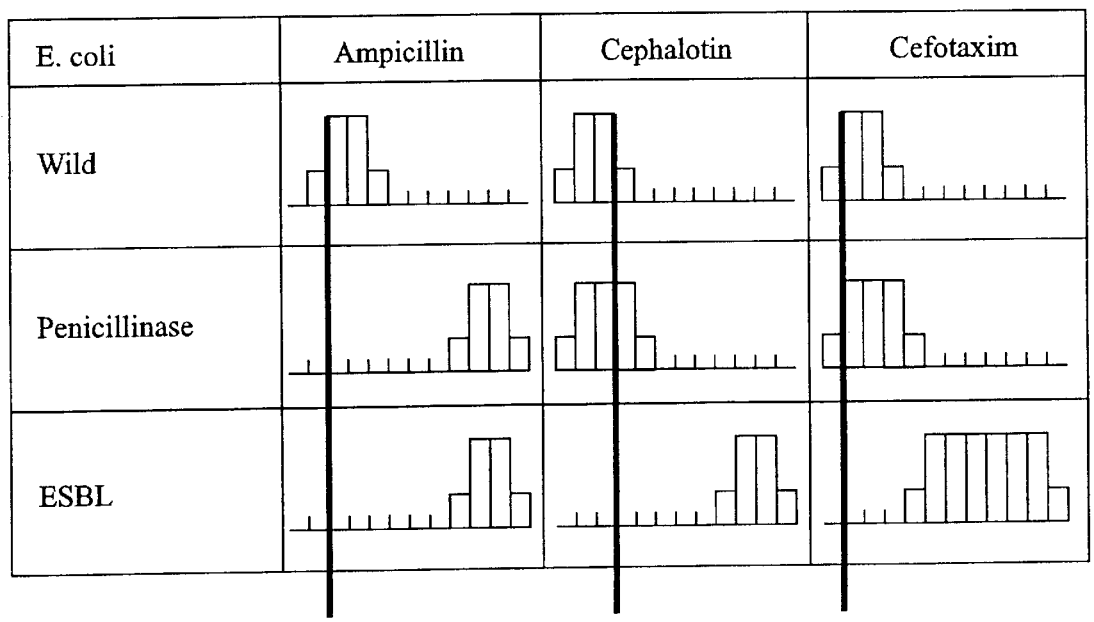
FIG. 2 illustrates a first analysis example according to the present invention, unambiguously indicating the resistance mechanism of a tested species.

FIG. 2 illustrates a main step of the method according to the present invention. By a conventional bacteriological test, a more or less accurate identification of the species to which the studied strain belongs is performed, for example, by means of biochemical identification reagents. This identification provides, for example, species *Escherichia coli*. At the same time, an antibiogram test is performed with a number of antibiotics. This antibiogram test provides a measurement of the MIC of the studied strain for different antibiotics, or enables locating this MIC in a given interval. In this example, Ampicillin, Cephalotin, and Cefotaxim are used.

Once the tests have been performed, a first step of the method consists in extracting from the database the MIC distributions associated with the resistance mechanisms of the identified species and with the tested antibiotics. The measured MICs, provided by the antibiograms and represented by vertical bars in the drawings, are then compared with the extracted MIC distributions. This comparison can be performed, for example, by making the normalized absolute frequency of the corresponding class of values in the distribution correspond to each measured MIC value. This normalized absolute frequency reflects the adequation of the measured MIC to the distribution extracted from the database.

The corresponding normalized absolute frequencies are then aggregated by resistance mechanism (for example, by calculating the average or the product of the normalized absolute frequencies), for all the tested antibiotics in a same family. This aggregation provides a synthetic indicator reflecting the adequation of the MIC measured for these antibiotics to each resistance mechanism.

If this synthetic indicator has a sufficiently high value for one of the resistance mechanisms, this resistance mechanism is the one to identify and the test is valid.

The simplified example of FIG. 2 shows that the resistance mechanism to identify is the "wild" mechanism, due to the fact that it is the only mechanism for which each measured MIC corresponds to a distribution associated to the wild mechanism.

In the situation where several resistance mechanisms have a sufficiently high indicator, only that or those having the highest indicators will preferably be kept.

Figure 3:
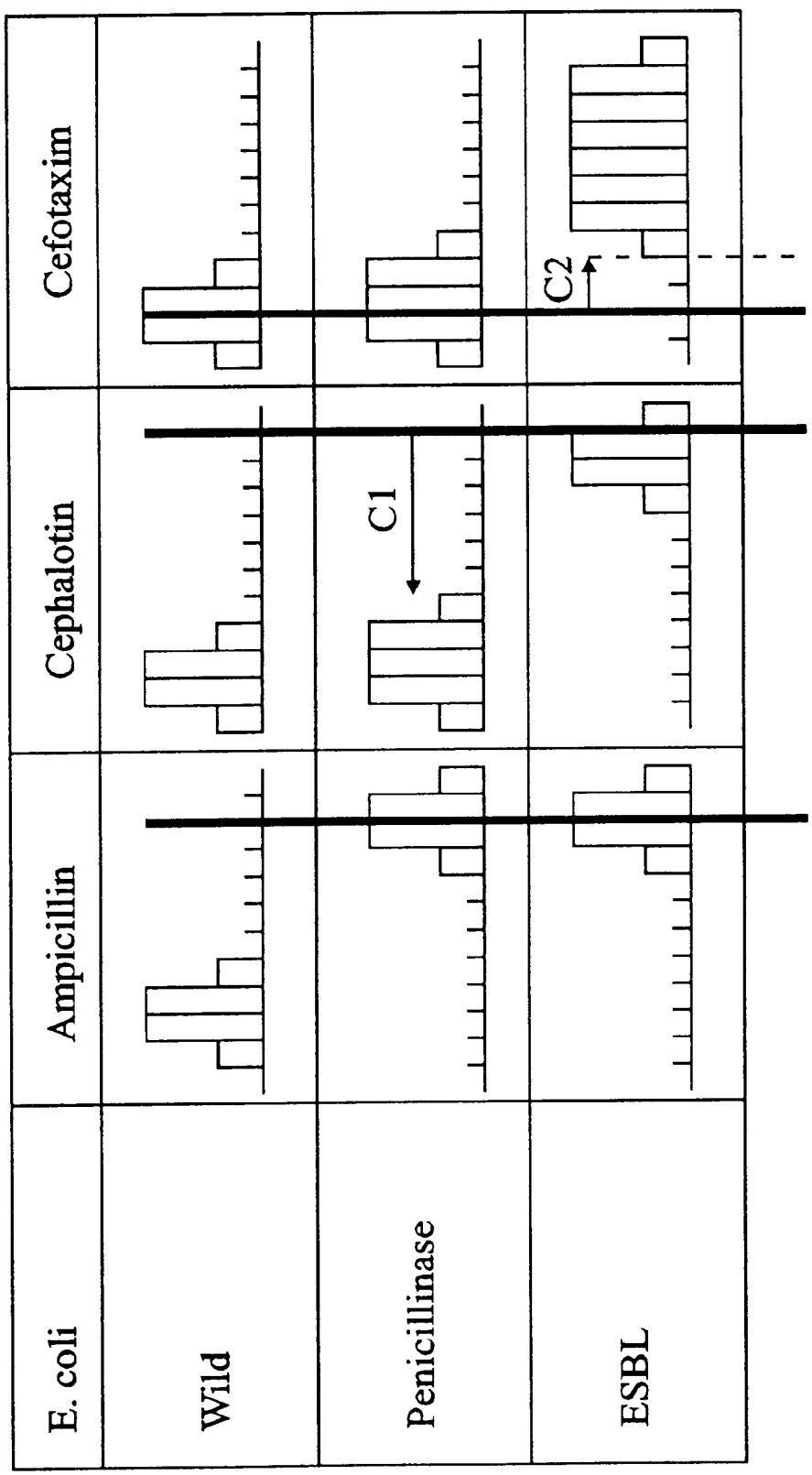
FIG. 3 illustrates an erroneous test case and a measurement correction proposal provided by the method according to the present invention.

FIG. 3 illustrates a situation, in the context of the example of FIG. 2, where the measured MICs do not identify any resistance mechanism. Indeed, for each resistance mechanism, at least one of the measured MICs is outside the corresponding MIC distribution.

In this case, the test is indicated as invalid. The method may then provide a correction for one or several of the measured MICs, by searching an optimal correction according to a number of criteria. It is in particular desired to minimize the number of corrected antibiotics, to minimize the number of downward corrections, to minimize the amplitude of the corrections, to maximize the adequation level of the uncorrected MICs to the used resistance mechanisms, to maximize the frequency at which these resistance mechanisms may be encountered. This optimizing may be performed by weighting the different criteria, or by submitting them to a hierarchy.

In the example of FIG. 3, the "wild" mechanism is excluded since two measured MICs out of three would have to be corrected. A resistance mechanism for which it is sufficient to correct a single measured MIC is sought in this example, so that all measured MICs correspond to the MIC distributions associated with this resistance mechanism.

If the resistance mechanism were "penicillinase", the measured MIC for Cephalotin should be shifted to the left by a value C1, i.e. decreased, to reach the upper limit of the missing MIC distribution.

If the resistance mechanism were "ESBL", the MIC measured for Cefotaxim should be shifted to the right by a value C2, i.e. increased, to reach the lower limit of the missing MIC distribution.

This latter correction C2 will be preferred, essentially for security reasons. Indeed, correction C2 is performed upwards, i.e. the species is stated more resistant to Cefotaxim than it seems to be with the measured MIC values. An upward correction will always be preferred to a downward correction. Of course, among several possible corrections, that of smaller amplitude will be preferred.

If more than three antibiotics are tested, corrections may be provided for more than one measured value, the number of corrected values having to remain limited.

The method also provides a correction of the identified species. Indeed, the species identification process always includes some error risk. The level of this risk depends in part on the identification method used, and in part on the involved species, some species having, with most usable methods, a non negligible risk of being mistaken with closely related species.

Figure 4:
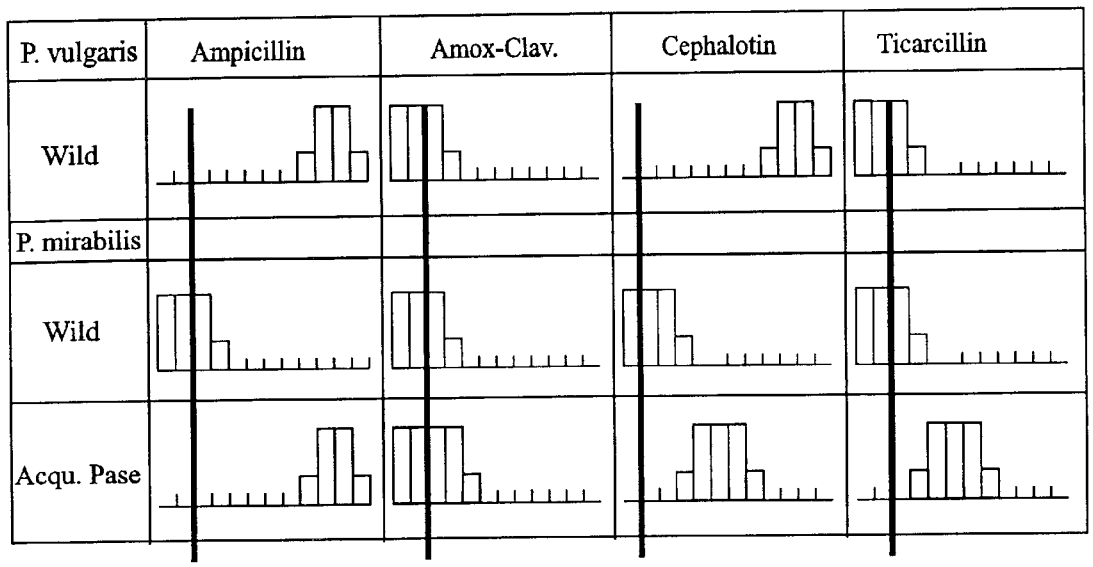
FIG. 4 illustrates an erroneous test case and a correction proposal for the species identification.

FIG. 4 illustrates such a proposal for correcting the species identification. The species was initially identified as "*Proteus vulgaris*", and the tested antibiotics are Ampicillin, Augmentin (Amoxicillin-Clavulanic acid), Cephalotin and Ticarcillin.

For this species, no resistance mechanism corresponds to the measured MICs. However, the database indexes a species, *Proteus mirabilis,* the wild resistance mechanism of which perfectly corresponds to the measured MICs. In this case, the system may suggest the *Proteus mirabilis* species having the "wild" resistance mechanism.

In most cases, other antibiotic families are tested (the drawings illustrate a single family). In these cases, before suggesting such a species correction, the system tries to identify additional resistance mechanisms for the other tested antibiotic families. A species is suggested only if one resistance mechanism per different antibiotic family can be identified. Preferably, the system will indicate the identified resistance mechanism(s) for the species suggested as a correction.

In the example of FIG. 4, it should be noted that the species suggested as a correction is of the same kind as the initially identified species. Generally, the system will suggest as a correction a species having a risk of confusion with the initially identified species.

To provide this type of correction, the database may contain, in particular, groups of species which may be mistaken. When no resistance mechanism is recognized for the initially identified species, the system searches a species preferentially in the corresponding group.

Figure 5:
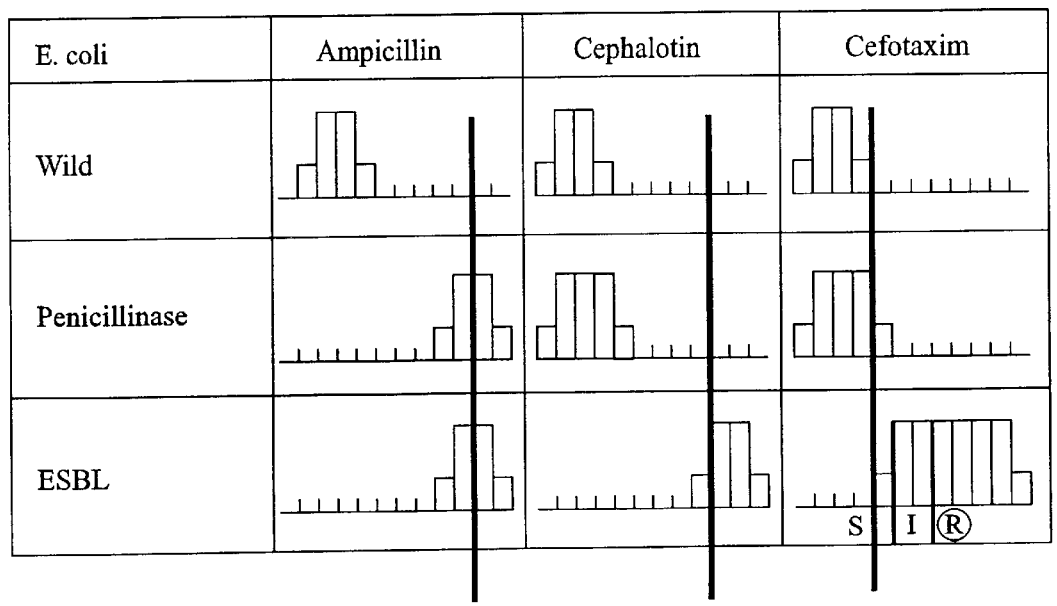
FIG. 5 illustrates a susceptibility statement correction based on information concerning a greater in vivo resistance of the tested species.

FIG. 5 illustrates the use of inconsistency information between the in vitro and in vivo susceptibilities, that can also be stored in the database.

In the example of FIG. 5, species *Escherichia coli* is tested again with Ampicillin, Cephalotin and Cefotaxim.

The measured MICs enable identifying the "ESBL" resistance mechanism. The MIC measured for Cefotaxim indicates that the species is rather susceptible. Now, research has shown that the strains having an "ESBL" resistance mechanism can be more resistant to Cefotaxim in vivo than in vitro. Some expert committees thus advocate that the species be stated resistant to Cefotaxim, even though measurements show it to be susceptible in vitro. Such advocating can further take into account the initially defined susceptibility category by comparing the MICs to the thresholds established by expert committees to define the "susceptible" and "resistant" categories. Thus, for some antibiotics and some resistance mechanisms, it may be advocated to turn into intermediate a category initially computed as susceptible, and to maintain categories initially computed as resistant.

Thus, for each antibiotic and each resistance mechanism of a species, the database may contain such an in vivo resistance information, which will be taken into account as soon as the tested antibiotic and the identified resistance mechanism correspond. The system also contains the rules for combining this information with the susceptibility categories defined on the basis of the thresholds.

Figure 6:
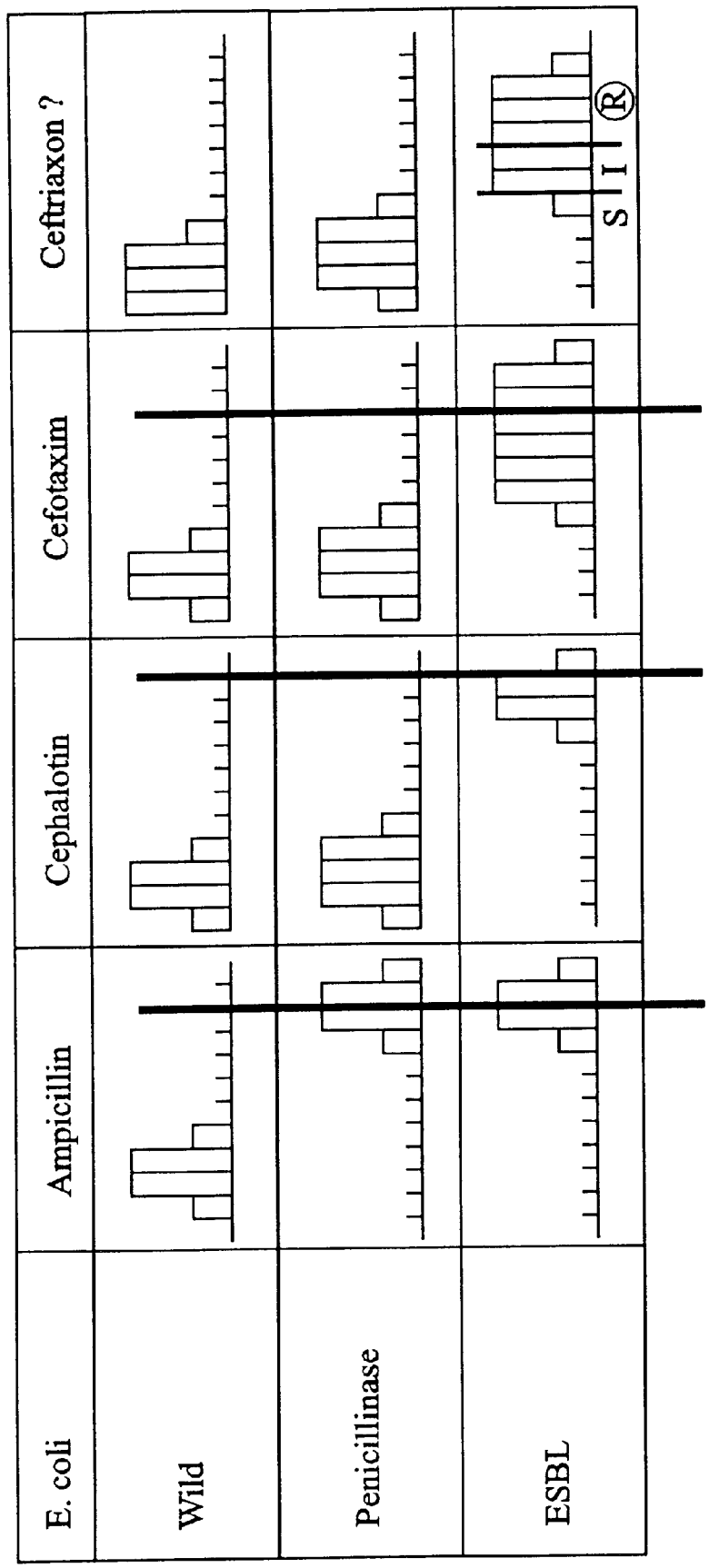
FIG. 6 illustrates a statement provided by the method according to the present invention concerning an untested antibiotic.

FIG. 6 illustrates the use of the information of database to provide additional indications. As in the preceding example, a strain identified as species *Escherichia coli* is tested with Ampicillin, Cephalotin and Cefotaxim. The method reveals the ESBL resistance mechanism.

Information may be desired on other currently used antibiotics to treat infections by *Escherichia coli,* such as Ceftriaxon.

The range in which the MIC of the studied strain for this antibiotic is probably located is deduced from the MIC distribution of Ceftriaxon for the strains of species *Escherichia coli* having an ESBL resistance mechanism, by only keeping the classes of MIC values for which the normalized absolute frequency exceeds a predetermined threshold. As a first intention, the susceptibility category of the studied strain can be determined by confronting the kept classes with the two thresholds established by expert committees to define the "susceptible", "intermediate", and "resistant" categories. Thus, the system will indicate the categories located on either side of each threshold included in the kept classes.

In the example of FIG. 6, all the distribution classes associated with the ESBL mechanism and with Ceftriaxon are kept. The two MIC thresholds are indicated by bold lines and are both included in the kept classes. The system then indicates all three "susceptible", "intermediate", and "resistant" categories.

Further, as for Cefotaxim, research has revealed that *Escherichia coli* with an ESBL mechanism may be resistant to Ceftriaxon in vitro. Thus, some experts advocate to state that this bacteria is resistant to Ceftriaxon, whatever the result of the in vitro MIC determination. The system may thus indicate that the bacterium is resistant to Ceftriaxon, even though Ceftriaxon has not been tested.

Generally, the system may provide an indication of the probable resistance level of the strain to the untested antibiotics, based on the MIC distribution for this antibiotic and the recognized resistance mechanism, and on the corresponding in vivo resistance information.

Of course, the present invention is likely to have various alterations, modifications and improvements which will readily occur to those skilled in the art. Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. A method carried out by a computer analysis system, of validating and interpreting test results of a micro-organism's susceptibility to antimicrobial agents, the method comprising the steps of:
    providing a database indexing resistance mechanisms of micro-organism species to antimicrobial agents of different antimicrobial agent families, the antimicrobial agents of each antimicrobial agent family having related biochemical structures and action modes, the database storing, for each resistance mechanism and antimicrobial agent, parameters characterizing a statistic distribution of minimum inhibitory concentrations;
    testing the micro-organism to generate a first test result that approximately identifies one of the micro-organism species to which the micro-organism belongs, and a second test result that measures minimum inhibitory concentrations of the micro-organism for each of the antimicrobial agents of the different antimicrobial agent families that are indexed to the identified species; and
    comparing the measured minimum inhibitory concentrations to the parameters characterizing the statistic distribution of minimum inhibitory concentrations for the resistance mechanisms of the identified species and the correspondingly indexed antimicrobial agent stored in the database to generate indicator values, each of the indicator values reflecting the adequacy of the corresponding measured minimum inhibitory concentrations;
    wherein if at least one of the indicator values is at or above a given threshold value, the first and second test results are valid, and if all the indicator values are below the given threshold value, at least one of the first and second test result is invalid.

2. The method of claim 1, wherein the parameters are selected from the group consisting of distribution average and standard deviation; distribution lower and upper limits and distribution shape; and normalized absolute frequency of values in the distribution.

3. The method of claim 2, wherein said distribution parameters stored in the database further include classes of minimum inhibitory concentration values and normalized absolute frequencies, the method further including, for an untested antimicrobial agent, the steps of:
    extracting from the database the classes and absolute frequencies associated with the resistance mechanism associated with an indicator value which is at or above the given threshold value;
    comparing the extracted classes, for which the absolute frequencies exceed the selected threshold, to see if they fall between two normalized MIC thresholds defining "susceptible", "intermediate", and "resistance" categories of a micro-organism; and
    including categories located on either side of each of the normalized thresholds located in the classes.

4. The method of claim 1, further comprising the step of identifying the resistance mechanism associated with the indicator value which is at or above the given threshold value.

5. The method of claim 4, wherein the database includes information about inconsistencies between in-vitro and in-vivo susceptibilities for the approximately identified species and the identified resistance mechanism, and if at least one of the indicator values is at or above the given threshold value, further comprising the steps of:
    determining from the information if there is a potential for the approximately identified species and the identified resistance mechanism to have an in-vivo resistance that is higher than an in-vitro resistance; and
    indicating when there is a potential for the approximately identified species and the identified resistance mechanism to have an in-vivo resistance that is higher than an in-vitro resistance.

6. The method of claim 1, wherein if all the indicator values are below the given threshold value and the second test result is invalid, further comprising the step of selecting corrections to be performed on at least one of the measured minimum inhibitory concentrations so that selected optimality criteria are met.

7. The method of claim 1, wherein if all the indicator values are below the given threshold value and the first test result is invalid, further comprising the steps of:
    selecting a different micro-organism species as a new first test result; and
    comparing the measured minimum inhibitory concentrations to the parameters characterizing the statistic distribution of minimum inhibitory concentrations for the resistance mechanisms of the selected identified species and the correspondingly indexed antimicrobial agent stored in the database to generate a new set of indicator values, each of the indicator values of the new set reflecting the adequacy of the corresponding measured minimum inhibitory concentrations;
    wherein if at least one of the indicator values is at or above a given threshold value, the new first test results is valid, and if all the indicator values are below the given threshold value, the new first test result is invalid and further comprising performing the selecting and comparing steps again.

* * * * *